US010899731B2

United States Patent
You et al.

(10) Patent No.: US 10,899,731 B2
(45) Date of Patent: Jan. 26, 2021

(54) PREPARATION OF FLUOROALKYL ELECTROCHROMIC POLYMERS AND THE USES THEREOF

(71) Applicant: AMBILIGHT INC., Milpitas, CA (US)

(72) Inventors: Liyan You, West Lafayette, IN (US); Jianguo Mei, West Lafayette, IN (US)

(73) Assignee: Ambilight Inc., Milpitas, CA (US)

( * ) Notice: Subject to any disclaimer, the term of this patent is extended or adjusted under 35 U.S.C. 154(b) by 0 days.

(21) Appl. No.: 16/586,148

(22) Filed: Sep. 27, 2019

(65) Prior Publication Data

US 2020/0102286 A1 Apr. 2, 2020

Related U.S. Application Data

(60) Provisional application No. 62/738,120, filed on Sep. 28, 2018.

(51) Int. Cl.

| | | |
|---|---|---|
| C07D 495/02 | (2006.01) |
| C07D 333/02 | (2006.01) |
| H01L 51/00 | (2006.01) |
| C07D 333/10 | (2006.01) |
| C07D 409/04 | (2006.01) |
| C07D 409/10 | (2006.01) |
| C08G 75/02 | (2016.01) |
| C08G 61/12 | (2006.01) |
| C07D 495/08 | (2006.01) |

(52) U.S. Cl.
CPC ......... *C07D 333/10* (2013.01); *C07D 409/04* (2013.01); *C07D 409/10* (2013.01); *C07D 495/08* (2013.01); *C08G 61/126* (2013.01); *C08G 75/0272* (2013.01); *C08G 2261/1332* (2013.01); *C08G 2261/3223* (2013.01)

(58) Field of Classification Search
CPC ............................ C07D 495/02; C07D 333/32
USPC ...................................... 549/50, 62; 313/498
See application file for complete search history.

(56) References Cited

U.S. PATENT DOCUMENTS

| 6,867,281 B2 | 3/2005 | Martin et al. | |
| 2004/0192942 A1* | 9/2004 | Huang et al. ........ | C07D 333/34 549/59 |
| 2007/0177243 A1* | 8/2007 | Liu et al. .................. | G02F 1/15 359/265 |
| 2019/0019957 A1* | 1/2019 | Hildebrandt et al. ..................... | H01L 51/0065 313/498 |

OTHER PUBLICATIONS

Alessandro Benedetto et al., "Fluorinated functionalized EDOT-based conducting films", Electrochimica Acta, vol. 53, pp. 3779-3788 (2008).

Irina Schwendeman et al., "Perfluoroalkanoate-Substituted PEDOT for Electrochromic Device Applications", Advanced Functional Materials, vol. 13, No. 7, Jul. 2003, pp. 541-547.

* cited by examiner

*Primary Examiner* — Charanjit Aulakh
(74) *Attorney, Agent, or Firm* — Sheppard Mullin Richter & Hampton LLP

(57) ABSTRACT

The present invention generally relates to electrochromic compounds and the uses thereof, particularly to series of fluoroalkyl 3,4-dioxythiophene compounds and their electrochromic polymers or co-polymers. Both compositions and process for manufacturing thereof are in the scope of this invention.

12 Claims, No Drawings

PREPARATION OF FLUOROALKYL ELECTROCHROMIC POLYMERS AND THE USES THEREOF

CROSS REFERENCE TO RELATED APPLICATION

This application claims benefits of U.S. provisional application No. 62/738,120 filed Sep. 28, 2018, entitled "PREPARATION OF FLUOROALKYL ELECTROCHROMIC POLYMERS AND THE USES THEREOF," the content of which is incorporated herein by reference in its entirety.

TECHNICAL FIELD

The present invention generally relates to electrochromic compounds and the uses thereof, particularly to series of fluoroalkyl 3,4-dioxythiophenes and their electrochromic polymers or co-polymers.

BACKGROUND

This section introduces aspects that may help facilitate a better understanding of the disclosure. Accordingly, these statements are to be read in this light and are not to be understood as admissions about what is or is not prior art.

Electrochromic polymers can change or adjust the intensity of visible light. Potential applications for electrochromic polymers can be found in different types of devices, such as e-paper, smart windows and anti-glare rearview mirror. Up to now, a lot of electrochromic polymers have been developed with different colors and structures. Most of efforts focus on the color and contrast of electrochromic polymers.

Propylenedioxythiophene (ProDOT) is a very good monomer to prepare high contrast electrochromic polymers. A large number of electrochromic polymers were made by ProDOT with different colors. However, thermal stability and chemical stability of ProDOT based polymer still need to increase. Semifluoroalkyl sidechain and perfluoroalkyl sidechain have been directly added on 3,4-ethoxylene dioxy thiophene (EDOT) to make Poly-3,4-ethoxylene dioxy thiophene (PEDOT) semiconduction polymers. However, due to the strong pi-pi packing, the electrochromic property of EDOT is not so good as ProDOT. The electrochromic contrast of PEDOT is much lower than ProDOT. Meanwhile, the electrochromic polymer resulting from EDOT can only have blue color. On the other hand, ProDOT can be easily copolymerized with other monomers to achieve different colors of the resulting electrochromic polymers. There are still unmet needs on electrochromic polymers that could provide high stability with diverse color variations.

Previous work in this includes electrochromic device by Schwendeman, C. L. et al., *Adv. Funct. Mater.* 13 (2003) 541; highly conducting and transparent thin films formed from new fluorinated derivatives of 3,4-ethylenedioxythiophene by Martin, B. D. et al., U.S. Pat. No. 6,867,281 B2, Mar. 15, 2005; and Alessandro B. et al., *Electrochimica Acta* 53 (2008) 3779-3788. Those references are incorporated into the current disclosure in their entirety.

These and other features, aspects and advantages of the present invention will become better understood with reference to the following detailed description and claims.

DETAILED DESCRIPTION OF EMBODIMENTS

While the concepts of the present disclosure are illustrated and described in detail in the description herein, results in the description are to be considered as exemplary and not restrictive in character; it being understood that only the illustrative embodiments are shown and described and that all changes and modifications that come within the spirit of the disclosure are desired to be protected.

In some illustrative embodiments, the present invention relates to a compound comprising the formula:

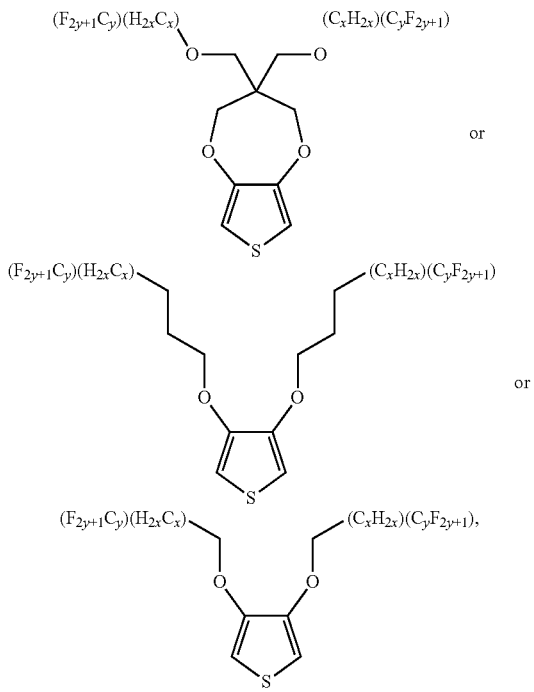

wherein x is an integer equal to or greater than 0 (with a range of 0 to about 20); y is an integer greater than 0 (with a range of 1 to about 40).

In some illustrative embodiments, the present invention relates to a compound comprising the formula:

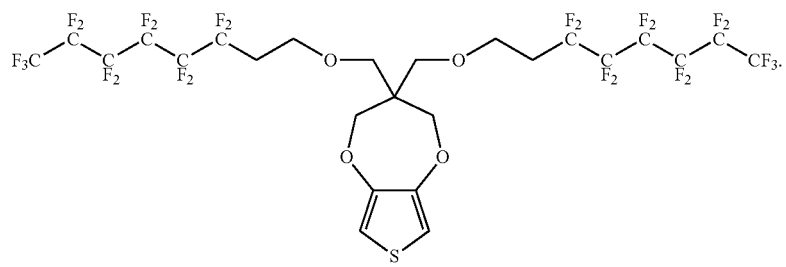 [SMILES: FC(F)(F)C(F)(F)C(F)(F)C(F)(F)C(F)(F)C(F)(F)CCOCC1(COCCC(F)(F)C(F)(F)C(F)(F)C(F)(F)C(F)(F)C(F)(F)F)COc2cscc2OC1]

In some illustrative embodiments, the present invention relates to a compound comprising the formula:

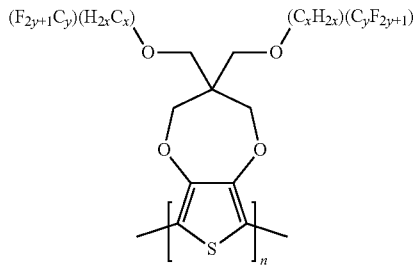

or

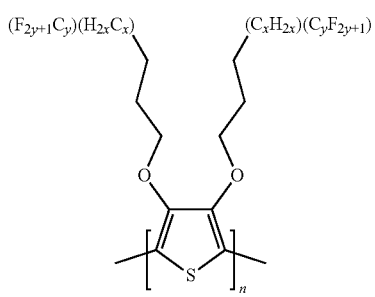

or

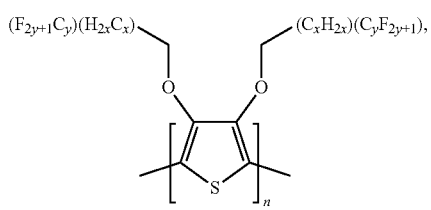

wherein n is an integer; x is an integer equal to or greater than 0 (with a range of 0 to about 20); y is an integer greater than 0 (with a range of 1 to about 40).

In some illustrative embodiments, the present invention relates to a compound comprising the formula:

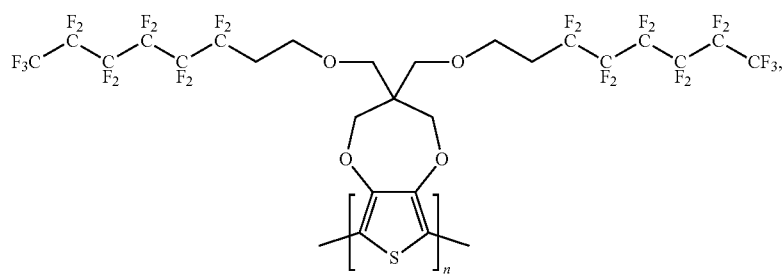

wherein n is an integer.

In some illustrative embodiments, the present invention relates to a compound comprising the formula:

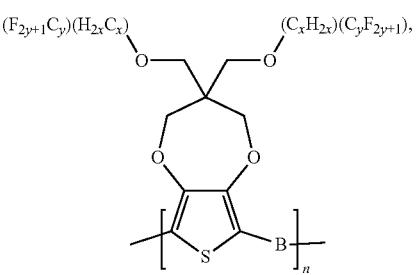

wherein n is an integer; x is an integer equal to or greater than 0 (with a range of 0 to about 20); y is an integer greater than 0 (with a range of 1 to about 40);

and B is selected from the group consisting of:

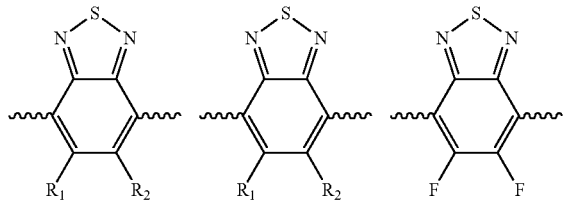

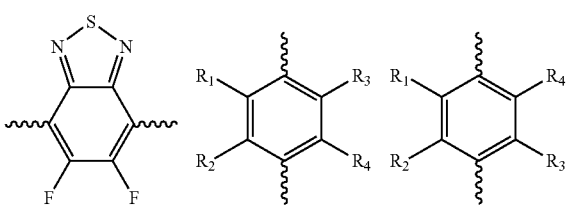

-continued
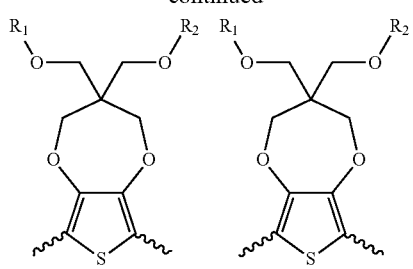
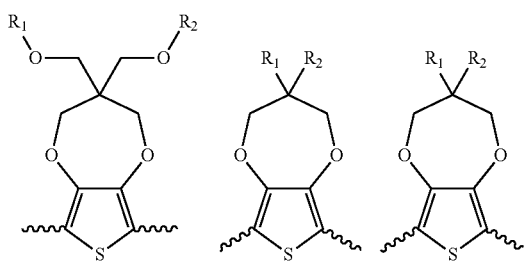
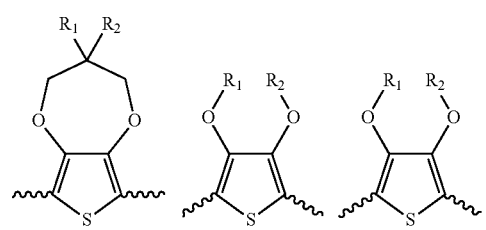
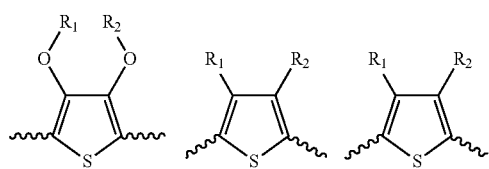
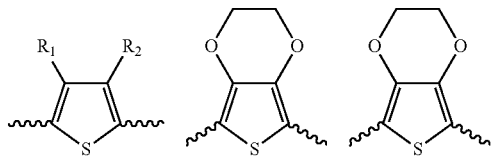
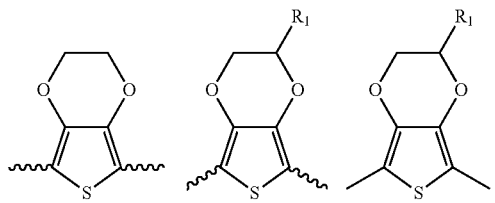
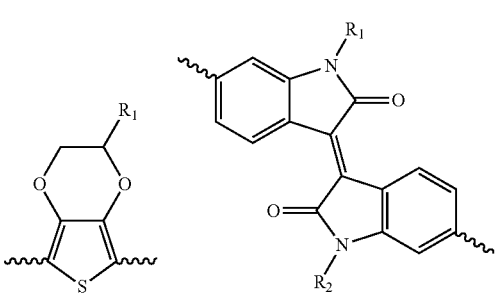
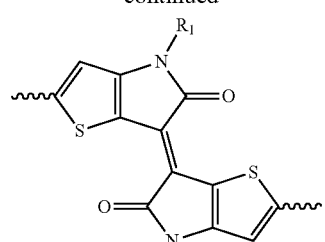
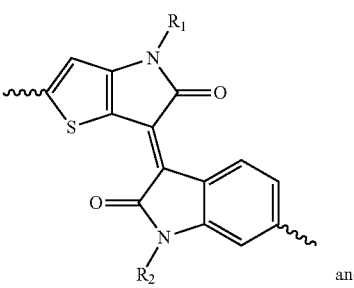
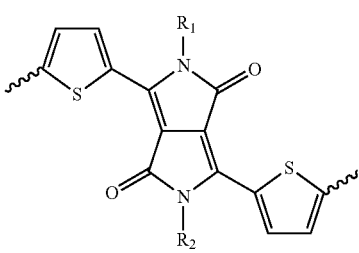
wherein the wave line ∽∽∽ represent the connecting points of the polymer unit;
and wherein B is incorporated into the polymer using a compound selected from the group comprising of:
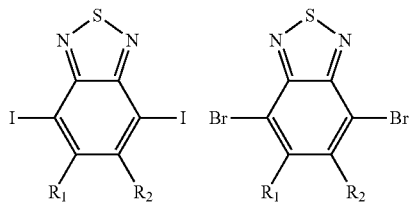
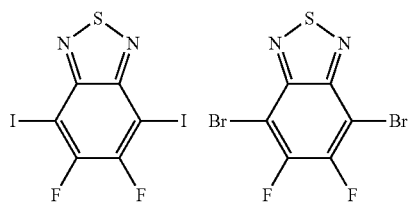
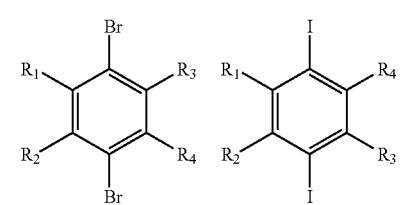

-continued

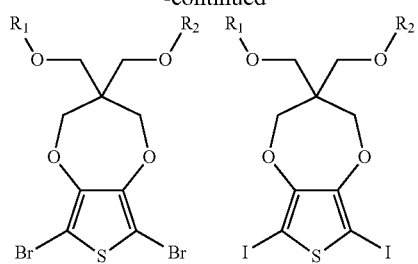
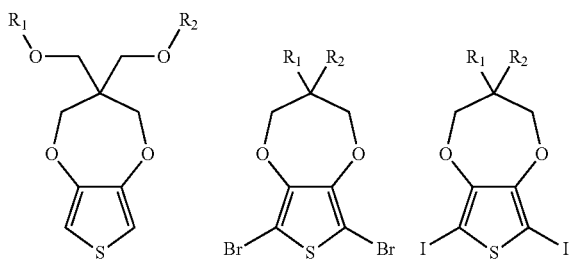
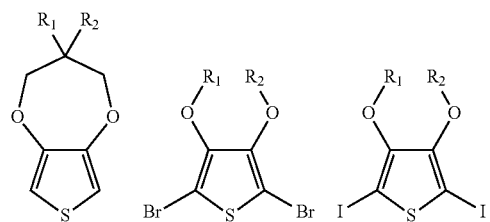
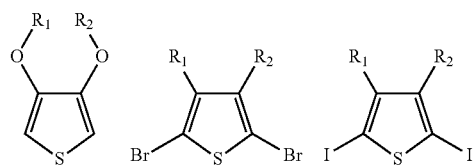
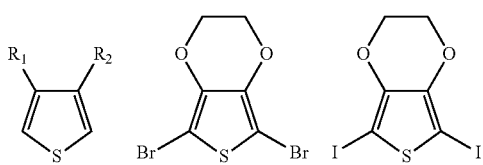
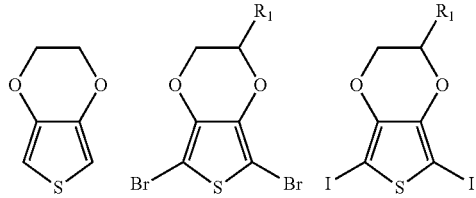
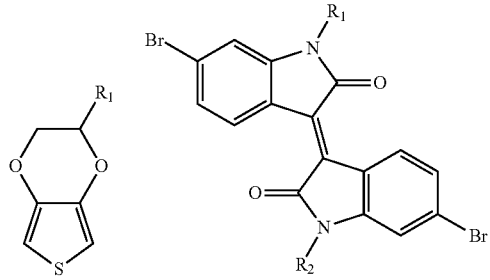

-continued

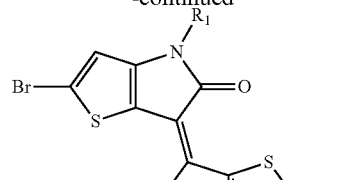
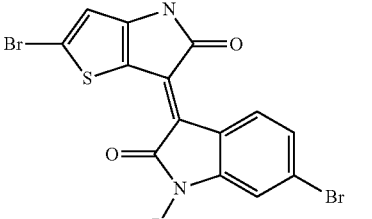
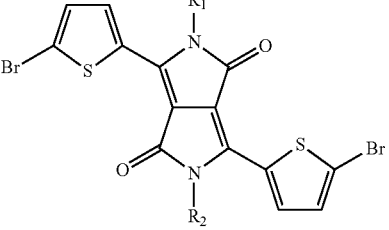
and
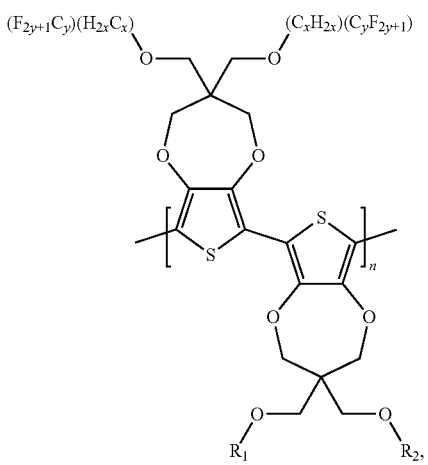

wherein $R_1$, $R_2$, $R_3$, $R_4$ can be independently selected from hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.

In some illustrative embodiments, the present invention relates to a compound comprising the formula:

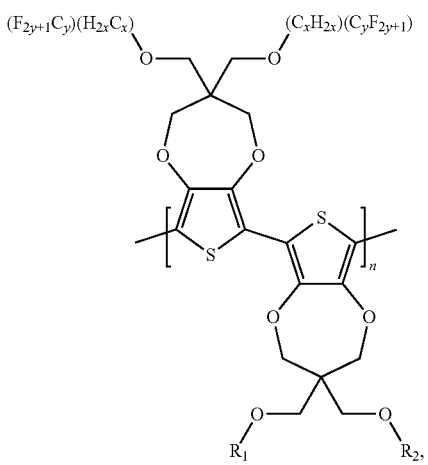

wherein n is an integer; x is an integer equal to or greater than 0 (with a range of 0 to about 20); y is an integer greater than 0 (with a range of 1 to about 40), wherein $R_1$, $R_2$, can be independently selected from hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.

In some illustrative embodiments, the present invention relates to a compound comprising the formula:

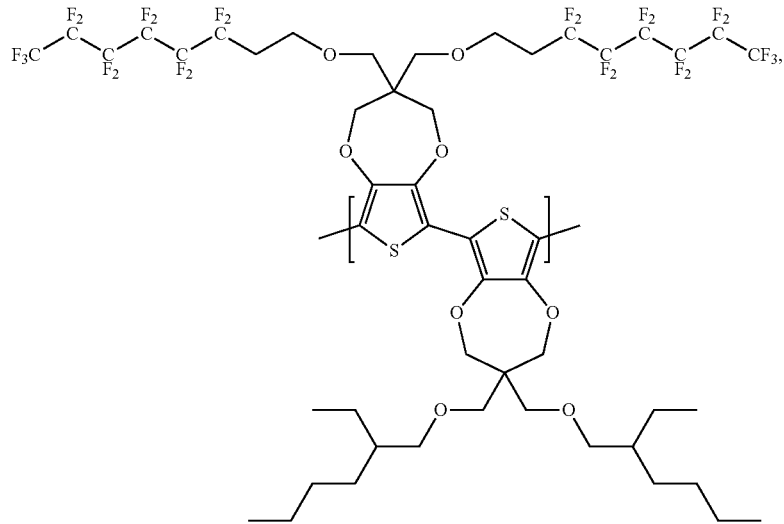

wherein n is an integer.

In some illustrative embodiments, the present invention relates to a compound comprising the formula:

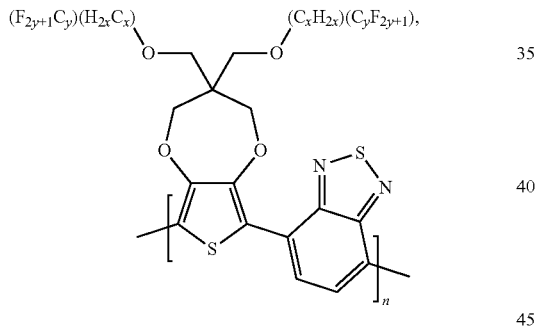

wherein n is an integer; x is an integer equal to or greater than 0 (with a range of 0 to about 20); y is an integer greater than 0 (with a range of 1 to about 40).

In some illustrative embodiments, the present invention relates to a compound comprising the formula:

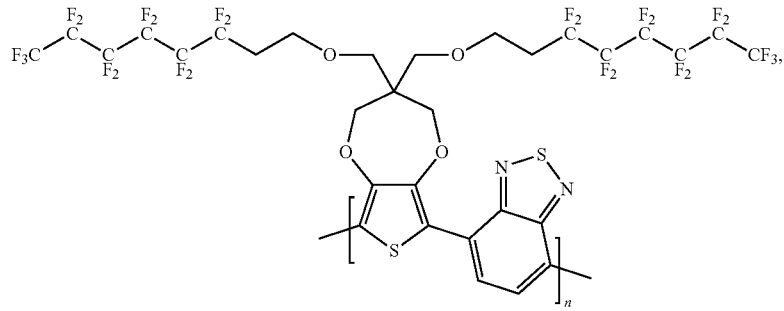

wherein n is an integer.

In some illustrative embodiments, the present invention relates to a compound comprising the formula:
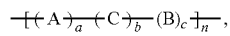
wherein a, b, c and n are an integer; x is an integer equal to or greater than 0 (with a range of 0 to about 20); y is an integer greater than 0 (with a range of 1 to about 40); A is
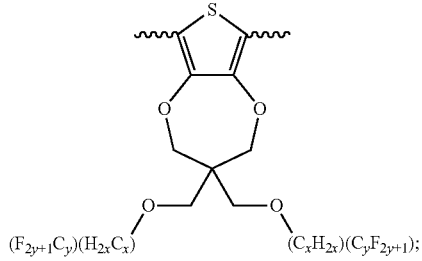
C is
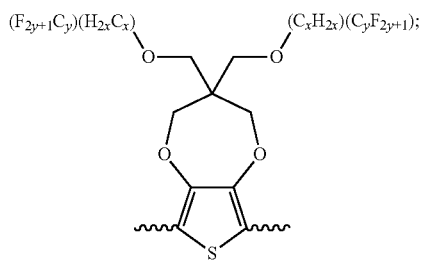
and
B is selected from the group consisting of:
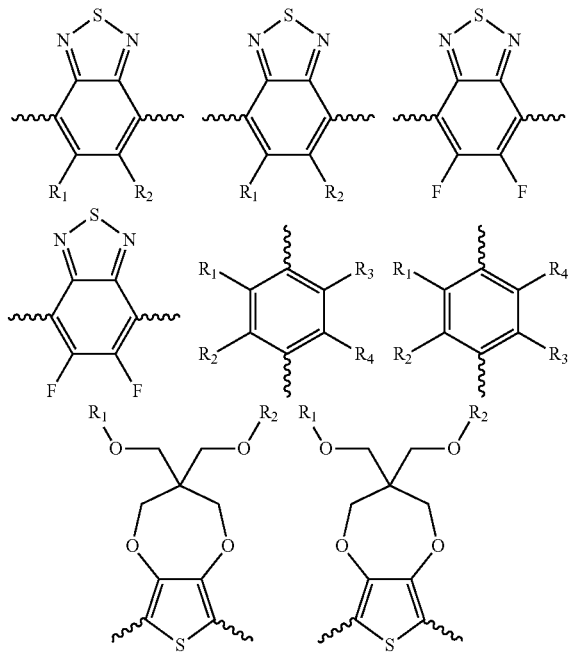
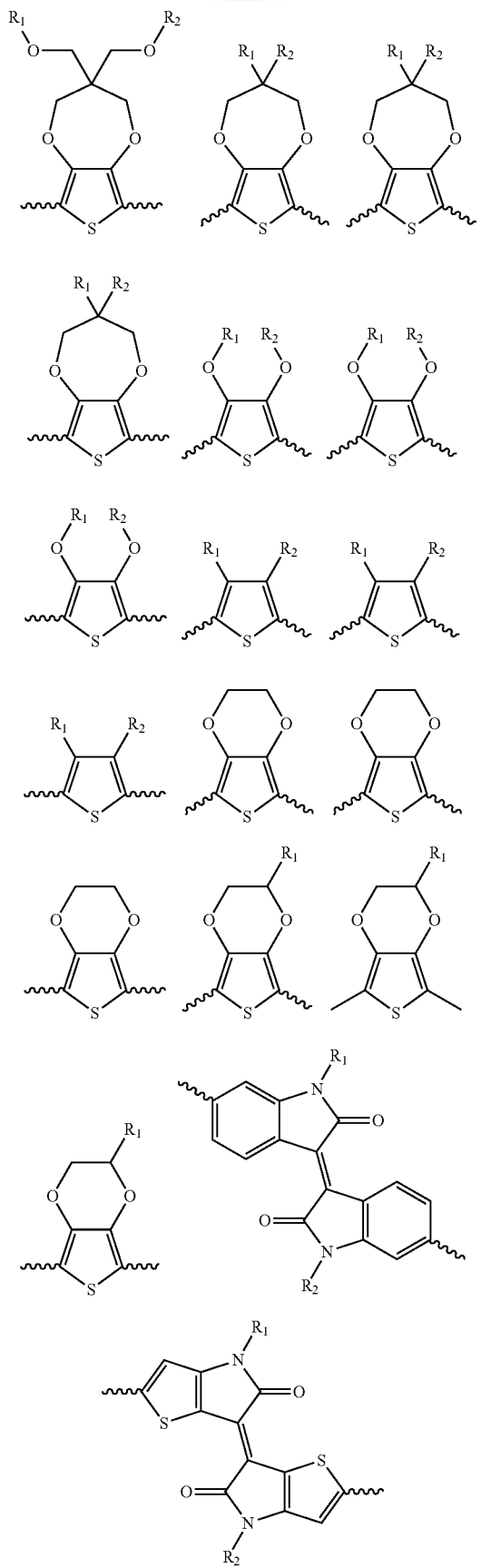

-continued
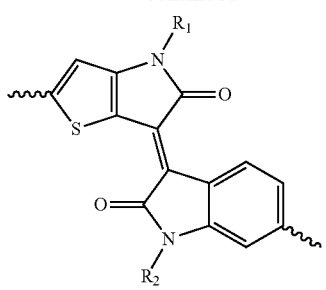
and
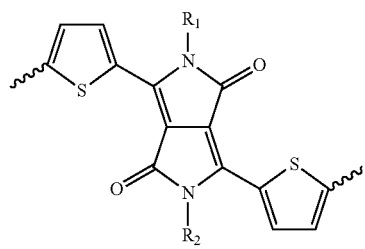
wherein the wave line ～ represent the connecting point of the polymer; wherein the blocks of A, B or C are not in any particular order; and
wherein B is incorporated into the polymer using a compound selected from the group comprising of:
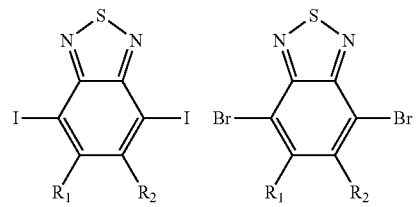
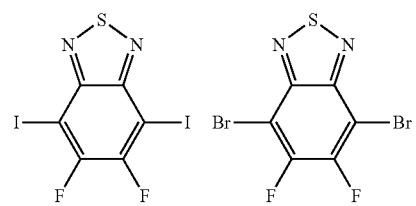
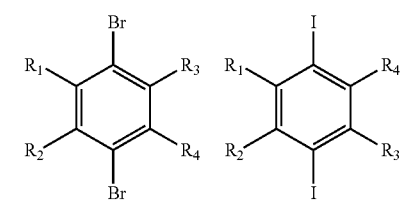
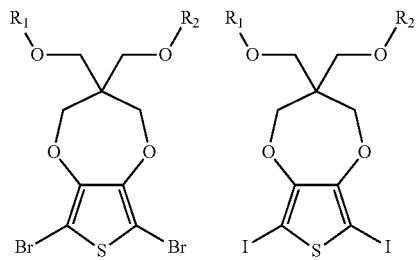
-continued
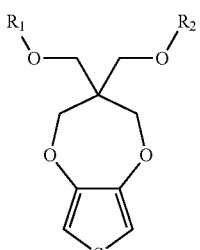
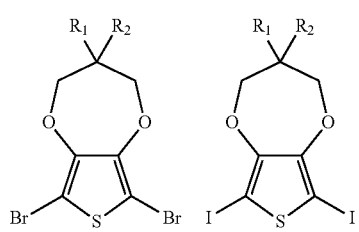
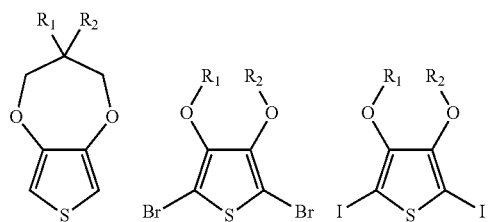
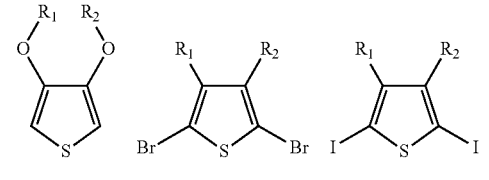
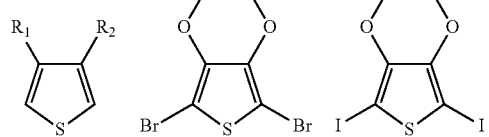
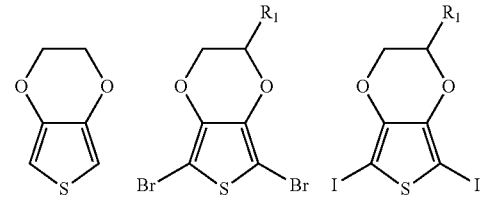
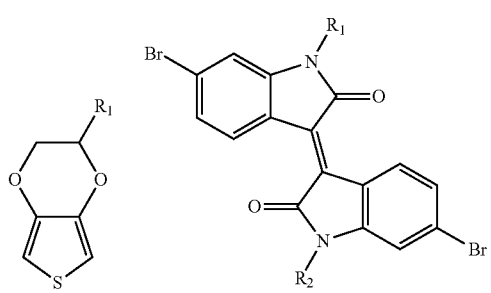

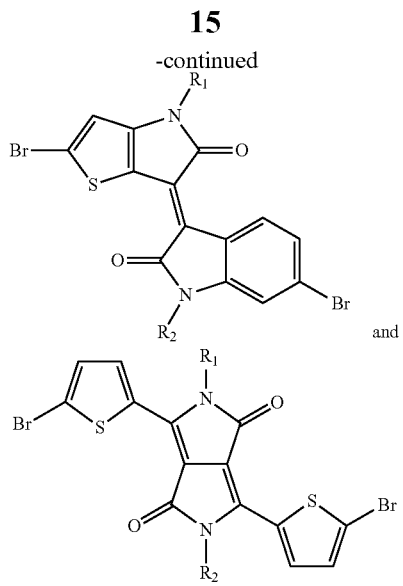

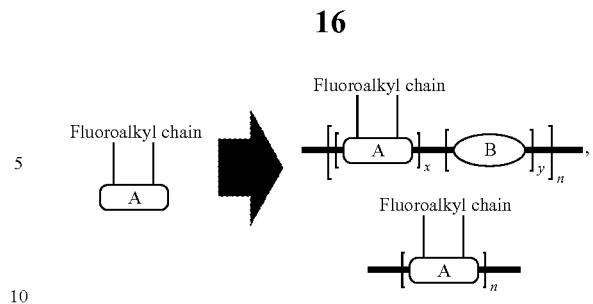

wherein Unit A is a fluoroalkyl sidechain monomer. Unit B is any other type of monomer which can form co-polymer with Unit A by polymerization reaction. With different types of Unit B and different ratios between Unit B and Unit A, we can achieve different colors and different electrochemical properties from the resulting electrochromic polymers. The x and y indicate the ratio of two units.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or wherein $R_1$, $R_2$, $R_3$, $R_4$ can be independently selected from hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.

In some illustrative embodiments, the present invention relates to a compound comprising the formula:

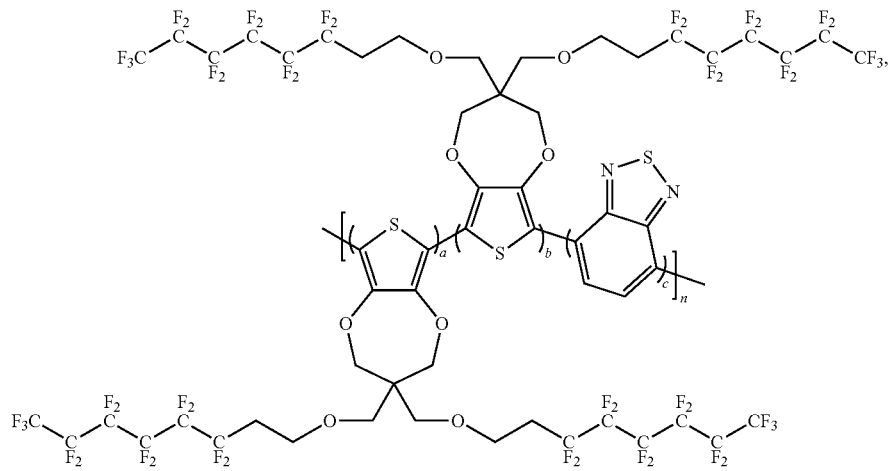

wherein a, b, c, and n are an integer.

In some illustrative embodiments, the present invention relates to a device or a machine incorporated the compound as disclosed herein.

In some illustrative embodiments, the present invention relates to a process to manufacture the compound as disclosed herein.

In some other illustrative embodiments, this present invention can be schematically described as range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 40 carbon atoms ($C_1$-$C_{40}$), 1 to 20 carbons ($C_1$-$C_{20}$), 1 to 10 carbon atoms ($C_1$-$C_{10}$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 40 carbon atoms ($C_2$-$C_{40}$), 2 to 20 carbons ($C_2$-$C_{20}$), 2 to 10 carbon atoms ($C_2$-$C_{10}$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms (C3-C8), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —$CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

Electrochromic polymers can change or adjust the intensity of visible light. Potential applications for electrochromic polymers can be found in different types of devices, such as e-paper, smart windows and anti-glare rearview mirror. Up to now, a lot of electrochromic polymers have been developed with different colors and structures. Most of efforts focus on the color and contrast of electrochromic polymers. However, one of the great challenge for electrochromic polymers comes from the chemical stability. Fluoropolymer is a polymer with multiple carbon-fluorine bonds which is high resistance to solvents, acids, and bases. The most known fluoropolymer is polytetrafluoroethylene (Teflon). After substituting C—H bond with stable C—F bond in polyethylene, the melting point increase from 130° C. to 327° C. At the same time the chemical stability can be greatly increased. Teflon often used in containers and pipework for reactive and corrosive chemicals. Another advantage of fluoropolymer is hydrophobic property. Most of fluoropolymer exhibit very large water contact angle due to the low surface energy. That means this kind of polymer can be resistant to the wetting of moisture. Since water is one of the main reasons to degrade the electrochromic polymers, this introduced hydrophobic property is highly desired to the electrochromic polymers.

The previously reported polymer (Schwendeman, C. L. et al., *Adv. Funct. Mater.* 13 (2003) 541) use perfluoroalkyl sidechain directly added on 3,4-ethoxylene dioxy thiophene (EDOT) to make poly-3,4-ethoxylene dioxy thiophene (PEDOT) electrochromic polymer. However, the electrochromic property of PEDOT is not so good as poly-propylenedioxythiophene (PProDOT). The electrochromic contrast of PEDOT is much lower than ProDOT. Meanwhile, the electrochromic polymer resulting from EDOT can only have blue color. On the other hand, ProDOT can be easily copolymerized with other monomers to achieve different colors of the resulting electrochromic polymers. Here, we introduce fluoroalkyl sidechains into propylenedioxythiophene (ProDOT) to make electrochromic polymers with fluoroalkyl sidechains. By doing so, we can intrinsically increase the chemical stability and moisture immunity of electrochromic polymers. When using different types of monomer B to make the copolymers, we can get different colors and different electrochemical properties of electrochromic polymers.

Here, by Williamson ether synthesis and radical reaction, we introduce fluoroalkyl sidechains into ProDOT to make electrochromic polymers with fluoroalkyl sidechain. The resulting fluoroalkyl substituted electrochromic polymers can intrinsically increase the hydrophobic property and chemical stability of electrochromic polymers. This fluoroalkyl substitution would not affect the tuning of different colors and electrochemical properties by selecting different types of monomer B to form the copolymer. This synthesis method can also be used for other types of fluoroalkyl monomers and polymer preparations.

Overall, when we introduce fluoroalkyl chain into electrochromic polymers, we can intrinsically increase the chemical stability of electrochromic polymers. At the same time, due to the hydrophobic nature of fluoroalkyl chain, the fluoroalkyl substituted electrochromic polymers can greatly increase the moisture immunity.

Scheme 1 shows the two major processes in preparing the starting materials for following polymerization process to manufacture the chromatic polymers or co-polymers,

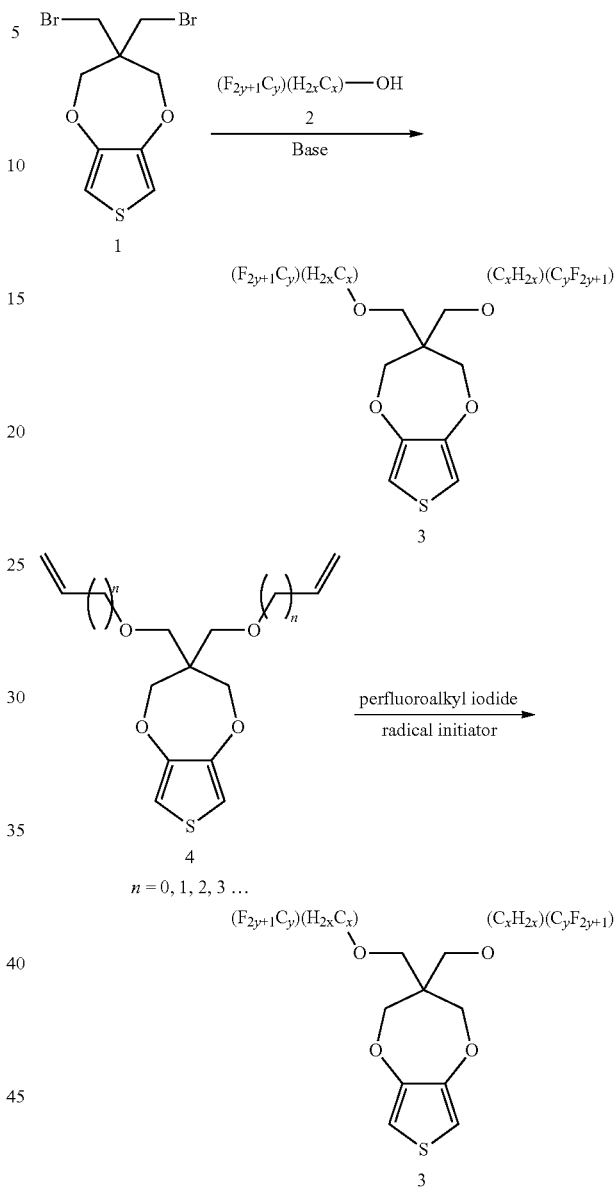

In scheme 1, the Base includes NaH, KH, nBuLi, tBuONa, tBuOK, $K_2CO_3$, $Cs_2CO_3$, Methyl magnesium bromide and all other Grignard reagent and base contained alkali metals; the radical initiator: 2,2'-Azobisisobutyronitrile, 2,2'-Azobisisoheptonitrile, Dibenzoyl peroxide, Triethylborane, Di-tert-butyl peroxide and all other Azo compounds, organic peroxides and Inorganic peroxides; and the general structure/formula for perfluoroalkyl iodide: $IC_yF_{2y+1}$ Herein, y is an integer greater than 0 (with a range of 1 to 40).

There are two methods to prepare propylenedioxythiophene (ProDOT) with fluoroalkyl sidechain. The first method uses 3,3-bis(bromomethyl)-3,4-dihydro-2H-thieno[3,4-b][1,4]dioxepine reacted with fluoroalkyl alcohol with the presence of a base. To a DMF solution, 2.0 equivalents of fluoroalkyl alcohol added into the flask followed by adding NaH (2.0 equivalents) and then the mixture is stirred for 2 hrs, then 1.0 equivalent of 3,3-bis(bromomethyl)-3,4-dihydro-2H-thieno[3,4-b][1,4]dioxepine is added slowly into the mixture. After reacting for 18 hrs at 100° C., water is added into the flask and the resulting solution is extracted with dichloromethane. The organic phase is applied to flash column and washed with dichloromethane (DCM)/hexane to get the product. The yield can range from 60 to 80%.

An example is shown in Scheme 2:

Scheme 2. Synthesis route 1 of monomer 3-A

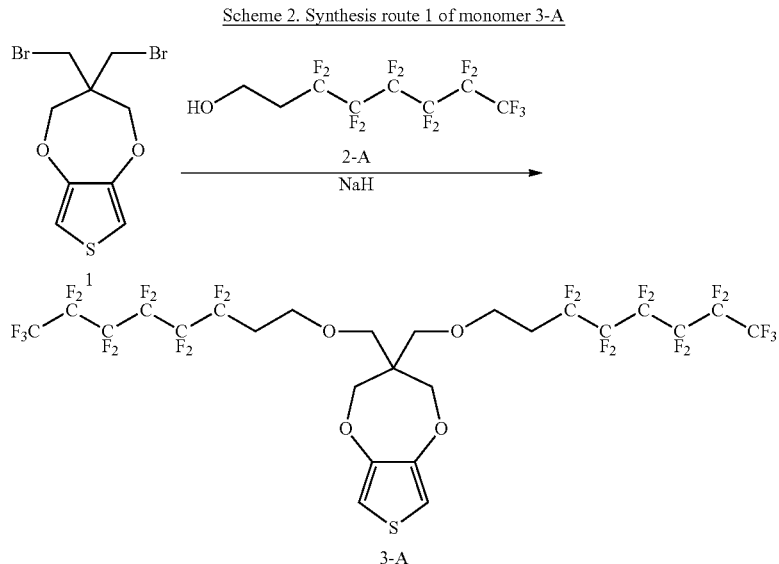

To a DMF solution, 3,3,4,4,5,5,6,6,7,7,8,8,8-tridecafluorooctan-1-ol (2.13 g, 5.85 mmol, 2.0 equivalents) is added into the flask followed by adding 60% NaH (234 mg, 5.85 mmol, 2.0 equivalents) and then the mixture is stirred for 2 hrs; then 3,3-bis(bromomethyl)-3,4-dihydro-2H-thieno[3,4-b][1,4]dioxepine (1.0 g, 2.92 mmol, 1.0 equivalent) is added slowly into the mixture. After reacting for 18 hrs at 100° C., water is added into the flask. The resulting solution is extracted with dichloromethane. The organic phase is applied to silica gel flash column and washed with dichloromethane (DCM)/hexane to obtain a product of about 2 g. The yield is about 75%.

The second method is to use propylenedioxythiophene (ProDOT) with a double bond sidechain as the starting material. Perfluoroalkyl iodide (2.0 equivalents) is added to a propylenedioxythiophene (ProDOT) (1.0 equivalent) in THF solution. Then azodiisobutyronitrile (0.2 equivalents) is added to the mixture, which is stirred under dark for 20 hours. After the reaction, water and dichloromethane are added sequentially to extract the product out. The resulting product solution is further purified by running through a silica gel column. The yield can range from 50 to 80%.

Scheme 3 below illustrates another route to form example monomer 3-A according to one example embodiment.

Scheme 3. Synthesis route 2 of monomer 3-A

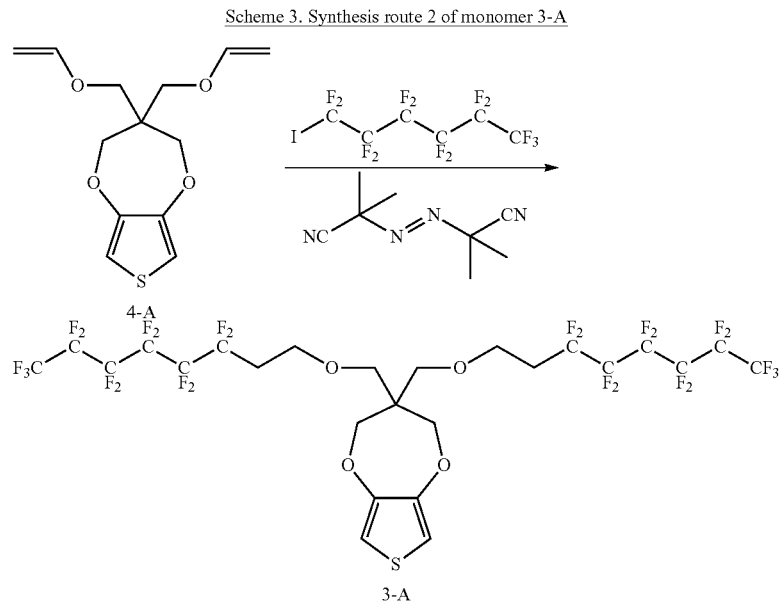

1,1,1,2,2,3,3,4,4,5,5,6,6-tridecafluoro-6-iodohexane (3.32 g, 7.45 mmol, 2.0 equivalents), 3,3-bis((vinyloxy)methyl)-3,4-dihydro-2H-thieno[3,4-b][1,4]dioxepine (ProDOT) (1 g, 3.73 mmol, 1.0 equivalent) are added to a THF solution. Then azodiisobutyronitrile (122 mg, 0.75 mmol, 0.2 equivalents) is added to the mixture, which is stirred under dark for 20 hours. After the reaction, water and DCM are added sequentially to extract the product out. The resulting product solution is further purified by running through a silica gel column with dichloromethane (DCM)/hexane to obtain about 1.7 g product. The yield is about 50%.

After we obtain the the fluoroalkyl sidechain monomers, we use direct arylation polymerization to prepare fluoroalkyl sidechain electrochromic polymers. When using different monomers B, we can either change the colors of polymers or adjust the ratios of fluoroalkyl sidechain in the polymers. The following four different examples (P-A, P-B, P-C and P-D) use different monomer B s, which result in four different electrochromic polymers with different colors and different ratios of fluoroalkyl sidechain.

Scheme 4 below illustrates a process to prepare polymer P-A according to one example embodiment.

Scheme 4. Preparation of polymer P-A

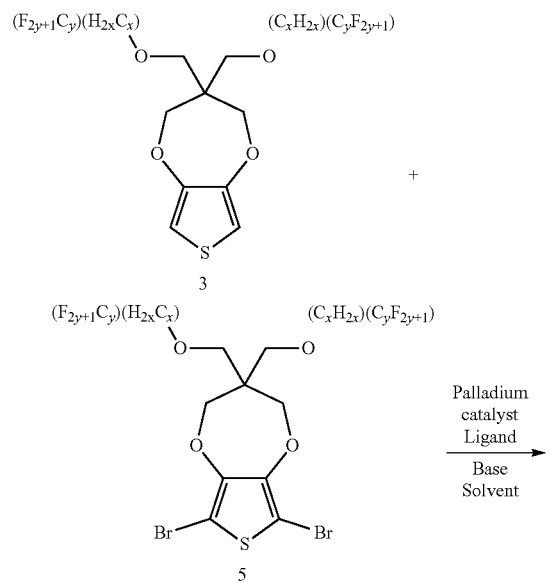

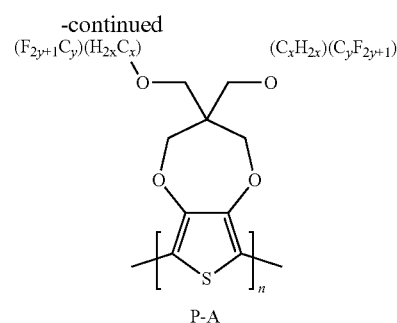

P-A

In Scheme 4 above, the palladium catalyst includes one or more of Palladium acetate, Bis(triphenylphosphine) palladium(II) dichloride, Tetrakis(triphenylphosphine) palladium (0), Tris(dibenzylideneacetone) dipalladium(0), Palladium chloride and all other palladium(II) or palladium(0) catalysts among others now known or later developed; The ligand includes one or more of Pivalic acid, Benzoic Acid, 2,2-Dimethylhexanoic acid, 2,2-dimethyl-heptanoic acid, 2,2-Dimethyloctanoic acid and all other organic acids without alpha hydrogen among others now known or later developed. The base includes one or more of Sodium Carbonate, Potassium carbonate, Cesium Carbonate and all other base contain alkali metals among others now known or later developed. The solvent is selected from one or more of Dimethylformamide, Dimethylacetamide, N-Methyl-2-pyrrolidone, Tetrahydrofuran, 2-Methyltetrahydrofuran, toluene, dimethylbenzene and all other polar aprotic solvents among others now known or later developed.

An example procedure is provided: To a schlenck tube are added fluoroalkyl sidechain propylenedioxythiophene (ProDOT) (1.0 equivalent), Dibromo-fluoroalkyl sidechain propylenedioxythiophene (ProDOT) (1.0 equivalent), $K_2CO_3$ (2.6 equivalent), PivOH (0.3 equivalent) and $Pd(OAc)_2$ (0.02 equivalent). The tube is kept under vacuum for about 15 minutes and then purged with $N_2$. The above process is repeated for three cycles. Then, nitrogen degassed N-Methyl pyrrolidone solvent is added into the tube, which is then heated to 140° C. for 20 hours under nitrogen. The hot reaction mixture is transferred to a 1:1 mixture solvent of $CH_3OH$ and 1M HCl with stirring. The mixture is filtered to obtain the solid content. The solid content is dissolved in chloroform and washed with 1M HCl solution. The organic phase is concentrated and precipitated with $CH_3OH$. The solution is then filtered and air dried to obtain polymer P-A. The yield ranges from 80 to 98%.

Scheme 5 below illustrates a process to prepare polymer P-A1 according to one example embodiment.

Scheme 5. Preparation of polymer P-A1

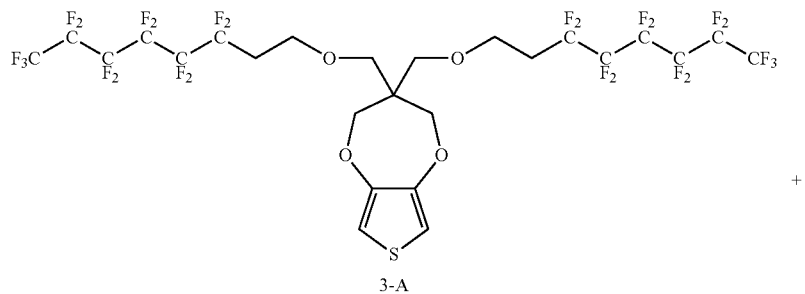

3-A

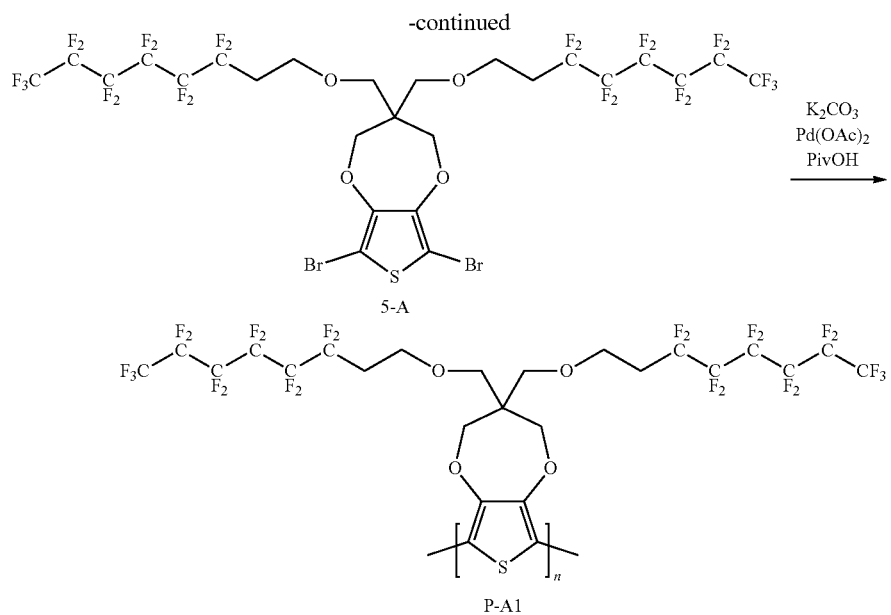

5-A

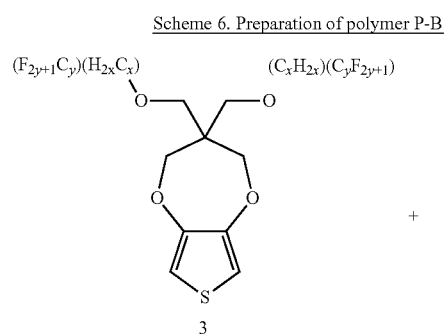

P-A1

To a schlenck tube are added 3,3-bis(((3,3,4,4,5,5,6,6,7,7,8,8,8-tridecafluorooctyl)oxy)methyl)-3,4-dihydro-2H-thieno[3,4-b][1,4]dioxepine (300 mg, 0.33 mmol, 1.0 equivalent), 6,8-dibromo-3,3-bis(((3,3,4,4,5,5,6,6,7,7,8,8,8-tridecafluorooctyl)oxy)methyl)-3,4-dihydro-2H-thieno[3,4-b][1,4]dioxepine (352 mg, 0.33 mmol, 1.0 equivalent), $K_2CO_3$ (119 mg, 0.86 mmol, 2.6 equivalent), PivOH (10.1 mg, 0.1 mmol, 0.3 equivalent) and $Pd(OAc)_2$ (1.5 mg, 0.007 mmol, 0.02 equivalent). The tube is kept under vacuum for about 15 minutes and then purged with $N_2$. The above process is repeated for three cycles. Then, nitrogen degassed N-Methyl pyrrolidone solvent 6 ml is added into the tube, which is then heated to 140° C. for 20 hours under nitrogen. The hot reaction mixture is transferred to a 1:1 mixture solvent of $CH_3OH$ and 1M HCl with stirring. The solution is filtered to obtain the solid content. The solid content is dissolved in chloroform and washed with 1M HCl solution. The organic phase is concentrated and precipitated with $CH_3OH$. The solution is filtered and air dried to get polymer P-A1 of about 0.55 g. The yield is about 92%.

Scheme 6 below illustrates a process to prepare polymer P-B according to one example embodiment.

Scheme 6. Preparation of polymer P-B

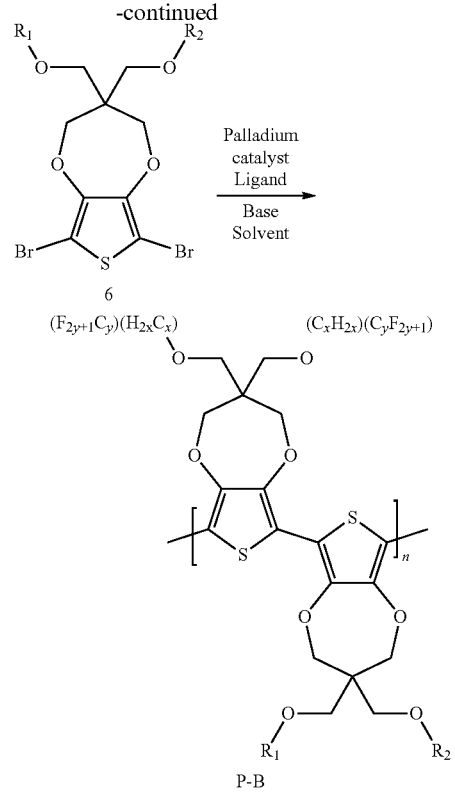

P-B wherein $R_1$, $R_2$ can be independently selected from hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.

To a schlenck tube are added fluoroalkyl sidechain propylenedioxythiophene (ProDOT) (compound 3) (1.0 equivalent), other sidechain dibromo-ProDOT (compound 6) (1.0 equivalent), $K_2CO_3$ (2.6 equivalent), PivOH (0.3 equivalent) and $Pd(OAc)_2$ (0.02 equivalent). The tube is kept under vacuum for about 15 minutes and then purged with $N_2$. The above process is repeated for three cycles. Then, nitrogen degassed N-Methyl pyrrolidone solvent is added into the tube, which is then heated to 140° C. for 20 hours under nitrogen. The hot reaction mixture is transferred to a 1:1 mixture solvent of $CH_3OH$ and 1M HCl with stirring. The solution is filtered to obtain the solid content. The solid content is dissolved in chloroform and washed with 1M HCl solution. The organic phase is concentrated and precipitated with $CH_3OH$. The solution is filtered and air dried to get polymer P-B. The yield ranges from 80 to 98%.

Scheme 7 below illustrates a process to prepare polymer P-B1 according to one example embodiment.

methyl)-3,4-dihydro-2H-thieno[3,4-b][1,4]dioxepine (198 mg, 0.33 mmol, 1.0 equivalent), $K_2CO_3$ (119 mg, 0.86 mmol, 2.6 equivalent), PivOH (10.1 mg, 0.1 mmol, 0.3 equivalent) and $Pd(OAc)_2$ (1.5 mg, 0.007 mmol, 0.02 equivalent). The tube is kept under vacuum for about 15 minutes and then purged with $N_2$. The above process is repeated for three cycles. Then, nitrogen degassed N-Methyl pyrrolidone solvent 6 ml is added into the tube, which is then heated to 140° C. for 20 hours under nitrogen. The hot reaction mixture is transferred to a 1:1 mixture solvent of $CH_3OH$ and 1M HCl with stirring. The solution is filtered to obtain the solid content. The solid content is dissolved in

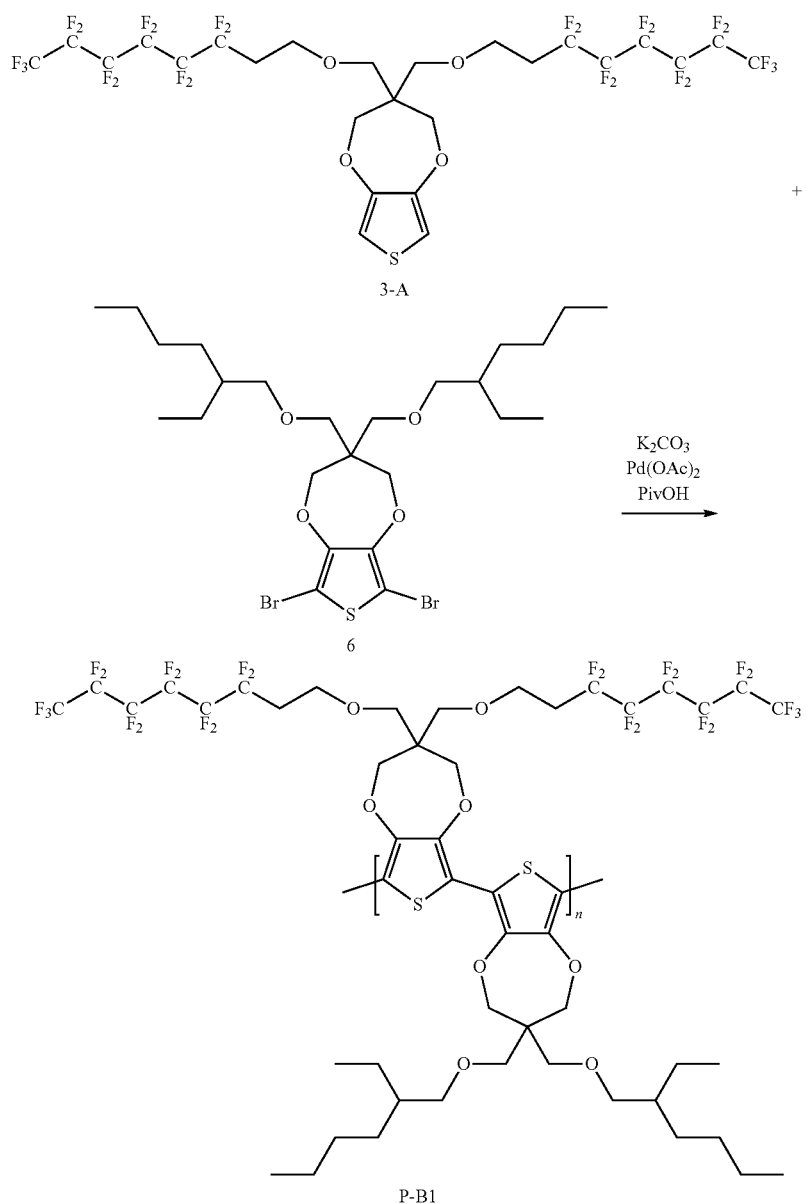

Scheme 7. Preparation of polymer P-B1

To a schlenck tube are added 3,3-bis(((3,3,4,4,5,5,6,6,7,7,8,8,8-tridecafluorooctyl)oxy)methyl)-3,4-dihydro-2H-thieno[3,4-b][1,4]dioxepine (300 mg, 0.33 mmol, 1.0 equivalent), 6,8-dibromo-3,3-bis(((2-ethylhexyl)oxy) chloroform and washed with 1M HCl solution. The organic phase is concentrated and precipitated with $CH_3OH$. The solution is filtered and air dried to get polymer P-B1 of about 0.39 g. The yield is about 87%.

Scheme 8 below illustrates a process to prepare polymer P-C according to one example embodiment.

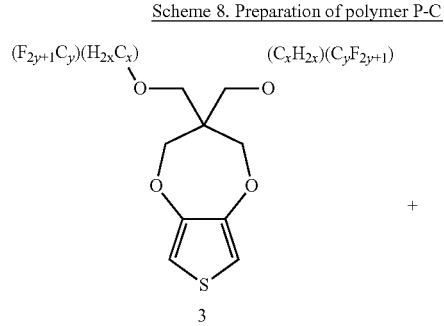

Scheme 8. Preparation of polymer P-C

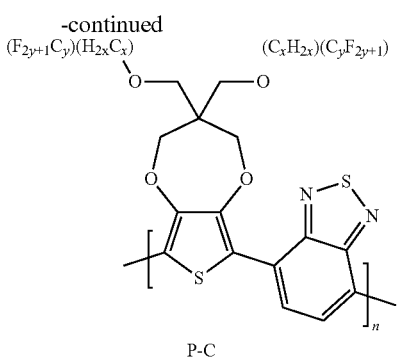

To a schlenck tube are added fluoroalkyl sidechain propylenedioxythiophene (ProDOT) (1.0 equivalent), 4,7-Dibromo-2,1,3-benzothiadiazole (1.0 equivalent), $K_2CO_3$ (2.6 equivalent), PivOH (0.3 equivalent) and $Pd(OAc)_2$ (0.02 equivalent). The tube is kept under vacuum for about 15 minutes and then purged with $N_2$. The above process is repeated for three cycles. Then, nitrogen degassed N-Methyl pyrrolidone solvent is added into the tube, which is then heated to 140° C. for 20 hours under nitrogen. The hot reaction mixture is transferred to a 1:1 mixture solvent of $CH_3OH$ and 1M HCl with stirring. The solution is filtered to obtain the solid content. The solid content is dissolved in chloroform and washed with 1M HCl solution. The organic phase is concentrated and precipitated with $CH_3OH$. The solution is filtered and air dried to get polymer P-C. The yield ranges from about 80 to 98%.

Scheme 9 below illustrates a process to prepare polymer P-C1 according to one example embodiment.

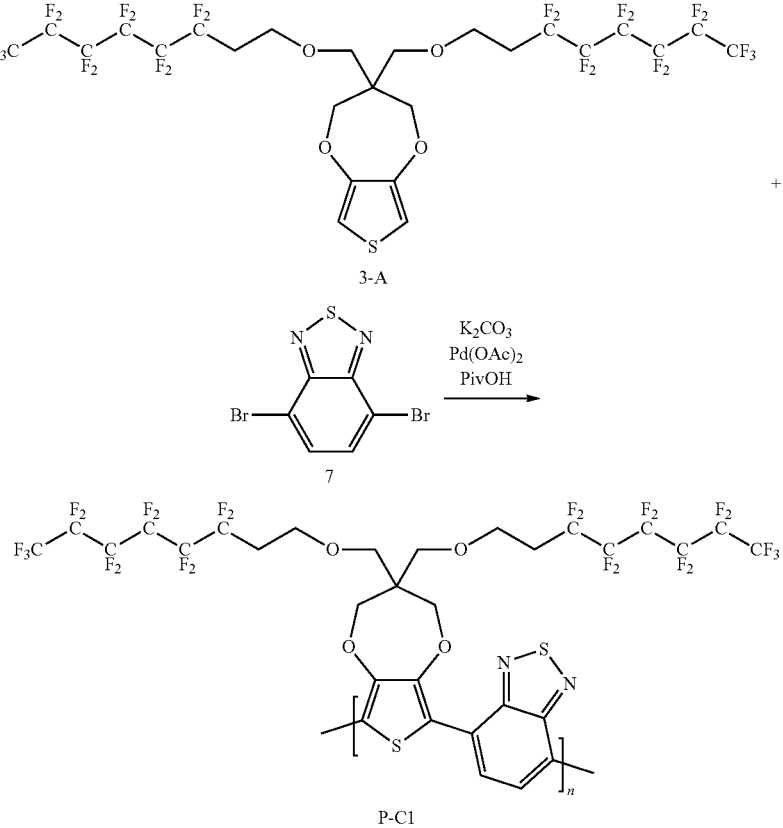

To a schlenck tube are added 3,3-bis(((3,3,4,4,5,5,6,6,7,7,8,8,8-tridecafluorooctyl)oxy)methyl)-3,4-dihydro-2H-thieno[3,4-b][1,4]dioxepine (300 mg, 0.33 mmol, 1.0 equivalent), 4,7-dibromobenzo[c][1,2,5]thiadiazole (97 mg, 0.33 mmol, 1.0 equivalent), K$_2$CO$_3$ (119 mg, 0.86 mmol, 2.6 equivalent), PivOH (10.1 mg, 0.1 mmol, 0.3 equivalent) and Pd(OAc)$_2$ (1.5 mg, 0.007 mmol, 0.02 equivalent). The tube is kept under vacuum for about 15 minutes and then purged with N$_2$. The above process is repeated for three cycles. Then, nitrogen degassed N-Methyl pyrrolidone solvent 6 ml is added into the tube, which is then heated to 140° C. for 20 hours under nitrogen. The hot reaction mixture is transferred to a 1:1 mixture solvent of CH$_3$OH and 1M HCl with stirring. The solution is filtered to get the solid content. The solid content is dissolved in chloroform and washed with 1M HCl solution. The organic phase is concentrated and precipitated with CH$_3$OH. The solution is filtered and air dried to get polymer P-C1 of about 0.33 g. Yield is about 93%.

Scheme 10 below illustrates a process to prepare polymer P-D according to one example embodiment.

Scheme 10. Preparation of polymer P-D

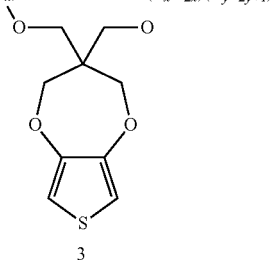

3

+

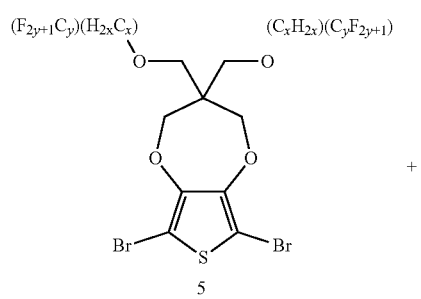

5

+

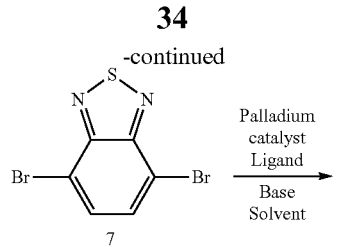

7

Palladium catalyst
Ligand
———————→
Base
Solvent

-continued

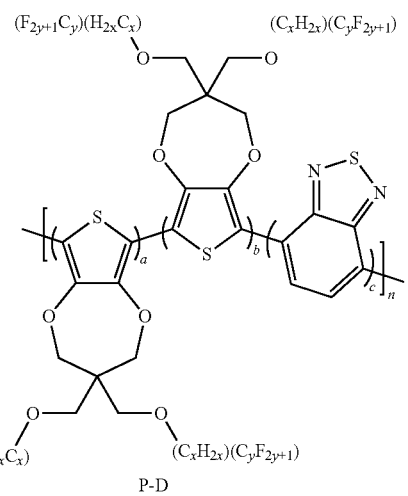

P-D

To a schlenck tube are added fluoroalkyl sidechain propylenedioxythiophene (ProDOT) (1.0 eq), Dibromo-fluoroalkyl sidechain propylenedioxythiophene (0.7 eq), 4,7-Dibromo-2,1,3-benzothiadiazole (0.3 eq), K$_2$CO$_3$ (2.6 eq.), PivOH (0.3 eq.) and Pd(OAc)$_2$ (0.02 eq.). The tube is kept under vacuum for about 15 minutes and then purged with N$_2$. The above process is repeated for three cycles. Then, nitrogen degassed solvent N-Methyl pyrrolidone is added into the tube, which is then heated to 140° C. for 20 hrs under nitrogen. The hot reaction mixture is transferred to a 1:1 mixture solvent of CH$_3$OH and 1M HCl with stirring. The solution is filtered to get the solid content. The solid content is dissolved in chloroform and washed with 1M HCl solution. The organic phase is concentrated and precipitated with CH$_3$OH. The solution is filtered and air dried to get polymer P-D. The yield ranges from 80 to 98%.

Scheme 11 below illustrates a process to prepare polymer P-D1 according to one example embodiment.

Scheme 11. Preparation of polymer P-D1

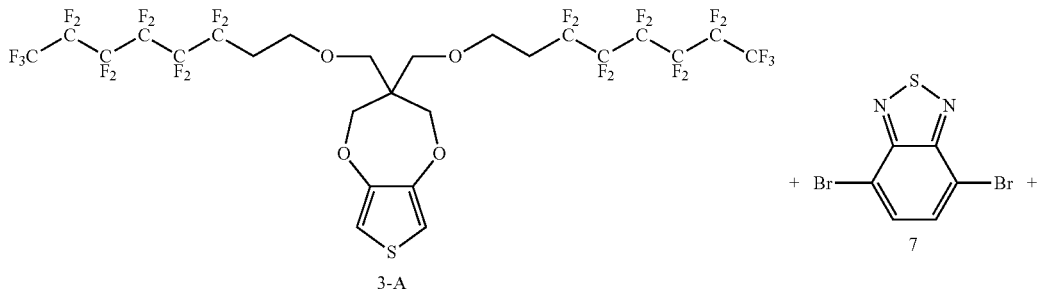

3-A

+ Br—[benzothiadiazole]—Br +

7

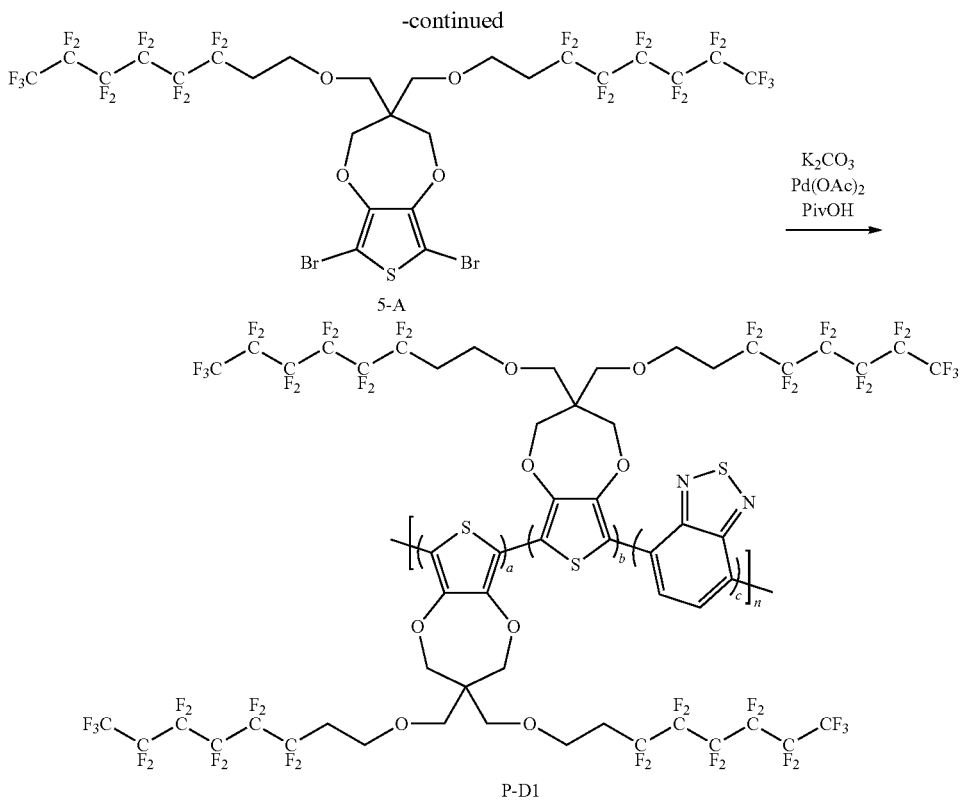

P-D1

To a schlenck tube are added 3,3-bis(((3,3,4,4,5,5,6,6,7,7,8,8,8-tridecafluorooctyl)oxy)methyl)-3,4-dihydro-2H-thieno[3,4-b][1,4]dioxepine (300 mg, 0.33 mmol, 1.0 equivalent), 4,7-dibromobenzo[c][1,2,5]thiadiazole (29.1 mg, 0.1 mmol, 0.3 equivalent), 6,8-dibromo-3,3-bis(((3,3,4,4,5,5,6,6,7,7,8,8,8-tridecafluorooctyl)oxy)methyl)-3,4-dihydro-2H-thieno[3,4-b][1,4]dioxepine (246.5 mg, 0.23 mmol, 0.7 equivalent), $K_2CO_3$ (119 mg, 0.86 mmol, 2.6 equivalent), PivOH (10.1 mg, 0.1 mmol, 0.3 equivalent) and $Pd(OAc)_2$ (1.5 mg, 0.007 mmol, 0.02 equivalent). The tube is kept under vacuum for about 15 minutes and then purged with $N_2$. The above process is repeated for three cycles. Then, nitrogen degassed N-Methyl pyrrolidone solvent 6 ml is added into the tube, which is then heated to 140° C. for 20 hours under nitrogen. The hot reaction mixture is transferred to a 1:1 mixture solvent of $CH_3OH$ and 1M HCl with stirring. The solution is filtered to get the solid content. The solid content is dissolved in chloroform and washed with 1M HCl solution. The organic phase is concentrated and precipitated with $CH_3OH$. The solution is filtered and air dried to get polymer P-D1 about 0.45 g. The yield is about 86%.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

We claim:
1. A compound having a formula of:

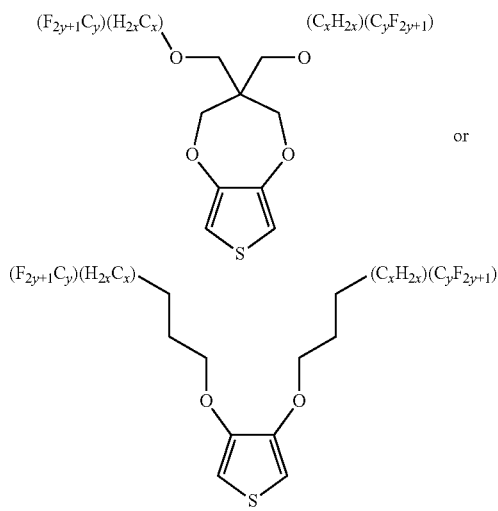

wherein x is an integer from, including, 0 to about 20; y is an integer from, including, 1 to about 40.

2. The compound of claim 1, wherein the compound has a formula of:

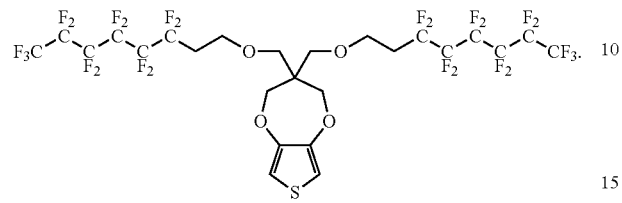

3. A polymer compound having a formula of:

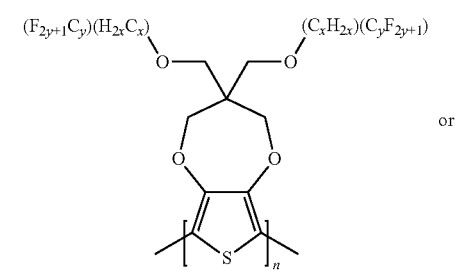

or

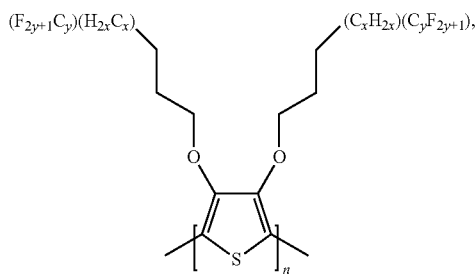

wherein n is an integer; x is an integer from, including, 0 to about 20; y is an integer from, including, 1 to about 40.

4. The polymer compound of claim 3, wherein the compound has a formula of:

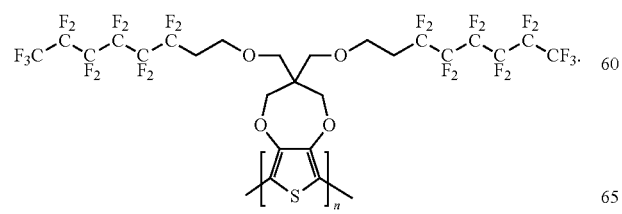

5. A polymer compound having a formula of:

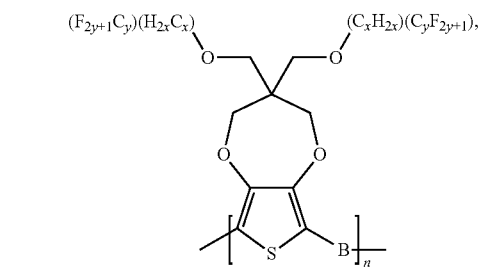

wherein n is an integer; x is an integer from, including, 0 to about 20; y is an integer from, including, 1 to about 40;

and B is selected from a group consisting of:

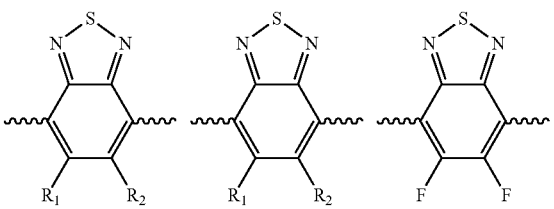

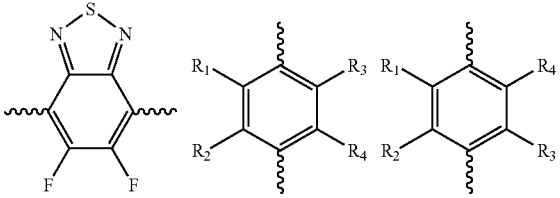

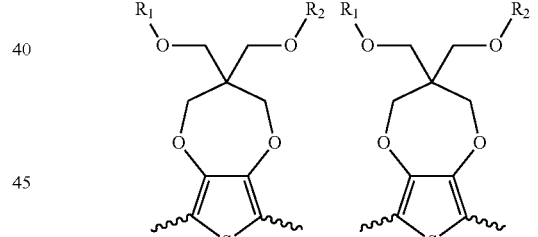

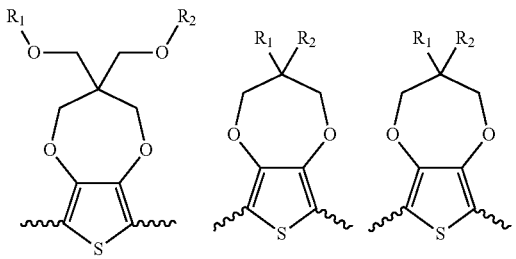

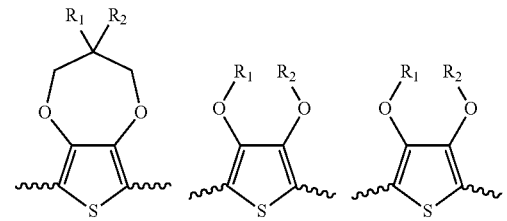

-continued
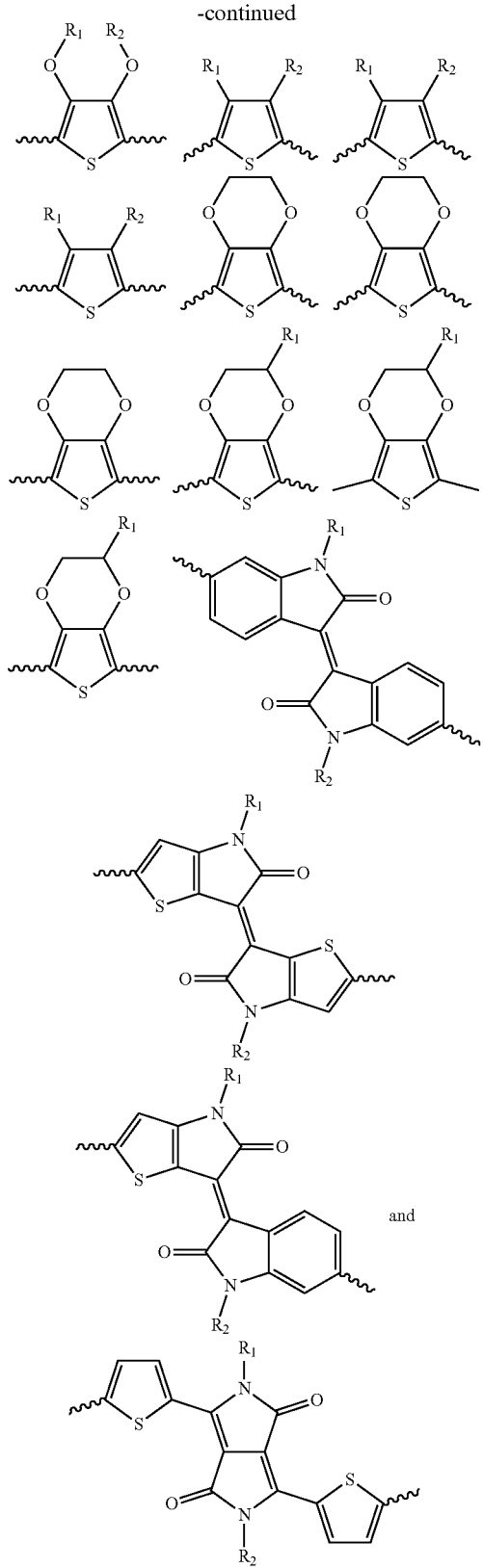
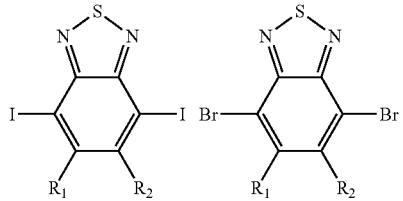
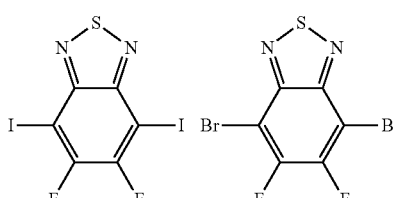
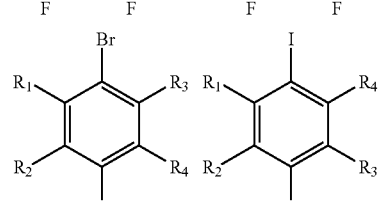
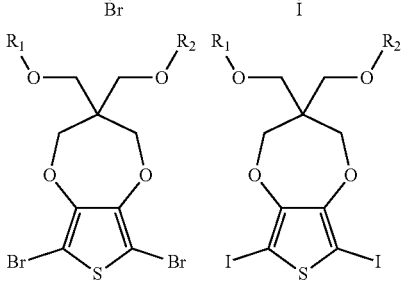
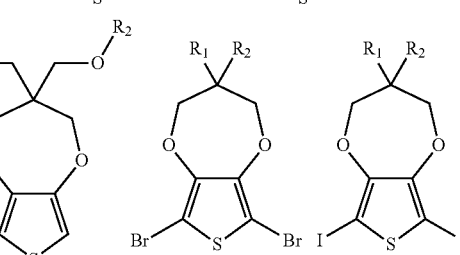
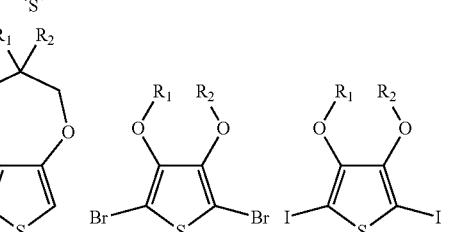
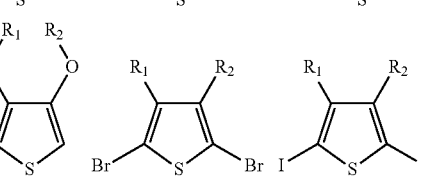
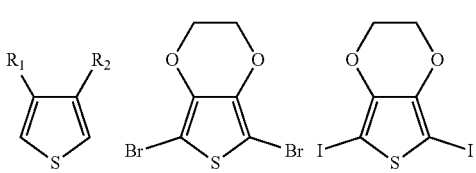
wherein the wave line ~~~~ represent connecting points of the polymer compound;
and wherein B is incorporated into the polymer compound using a compound selected from a group comprising of:

-continued

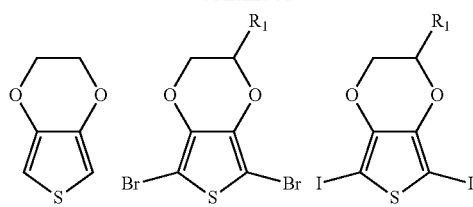

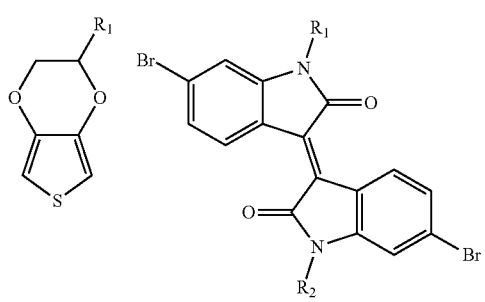

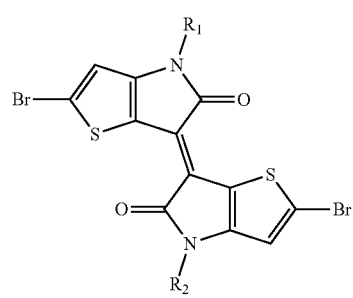

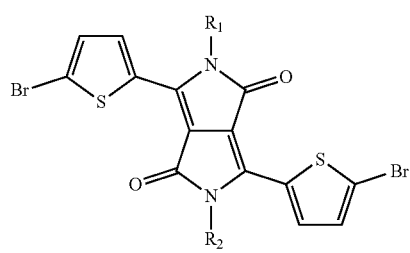

wherein each of $R_1$, $R_2$, $R_3$, $R_4$ is selected from one of hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.

6. The polymer compound of claim 5, wherein the polymer compound has a formula of:

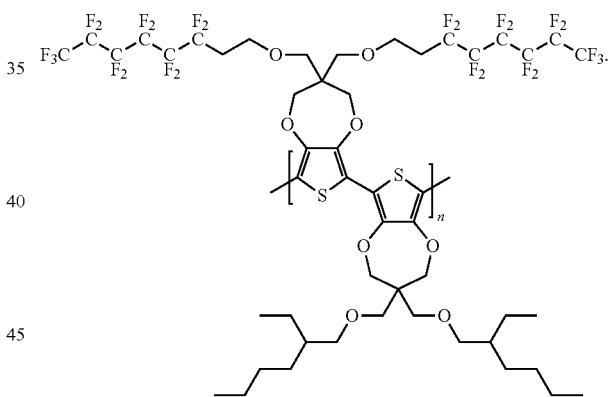

wherein each of $R_1$, $R_2$ is selected from one of hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.

7. The polymer compound of claim 6, wherein the polymer compound has a formula of:

8. The polymer compound of claim 5, wherein the polymer compound has a formula of:

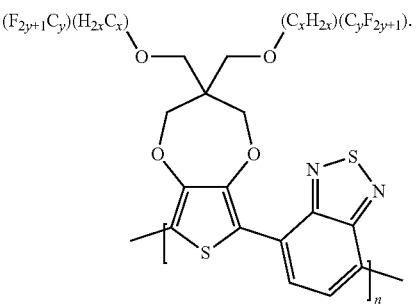

9. The polymer compound of claim 8, wherein the polymer compound has a formula of:
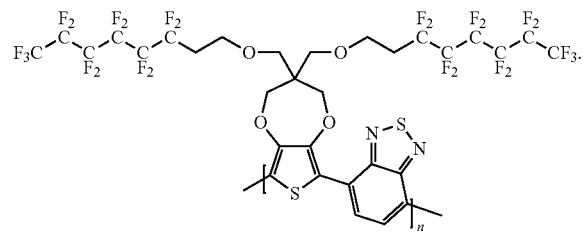
10. A polymer compound having comprising a formula of:
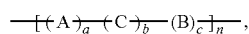
wherein a, b, c and n are an integer; x is an integer from, including, 0 to about 20; y is an integer from, including, 1 to about 40;
A is
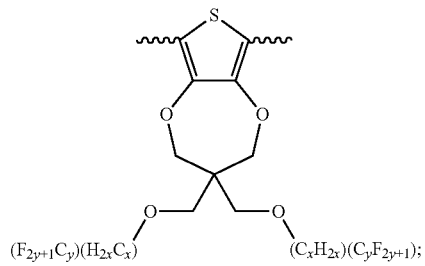
C is
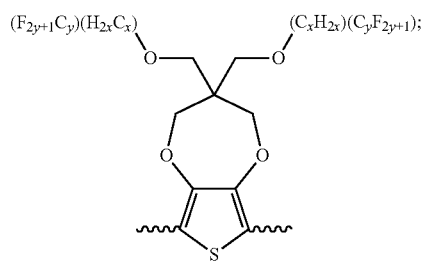
and
B is selected from a group consisting of:
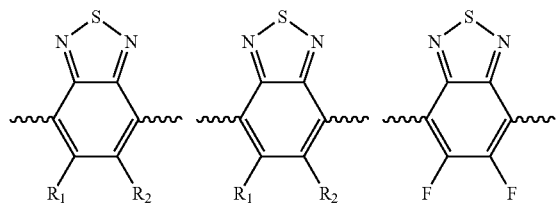
-continued
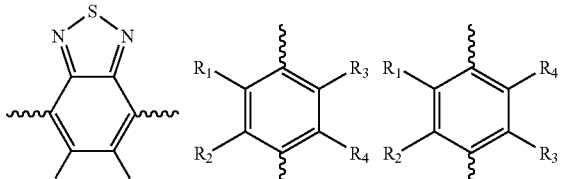
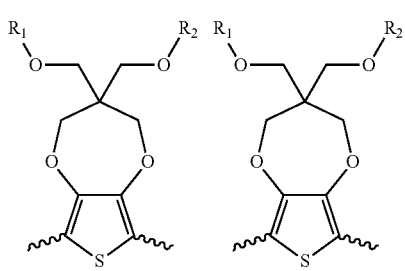
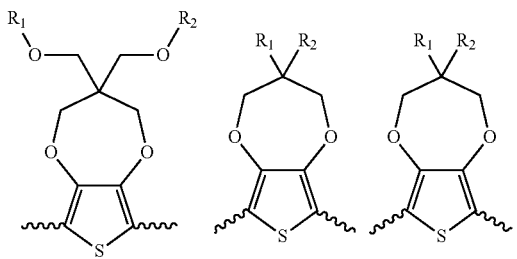
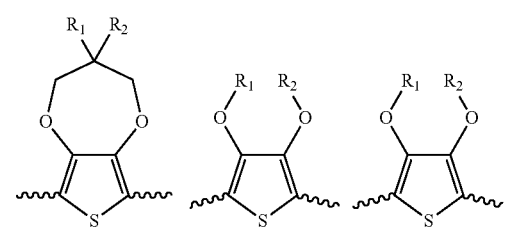
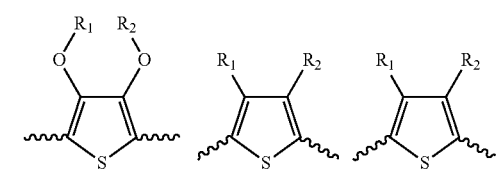

-continued
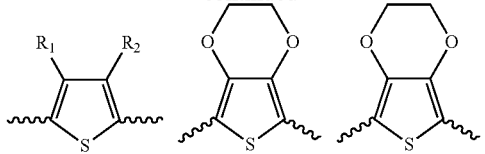
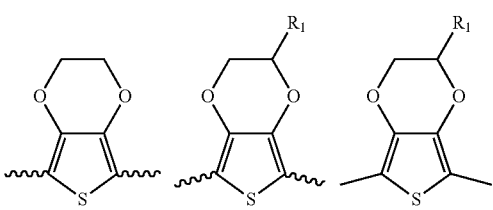
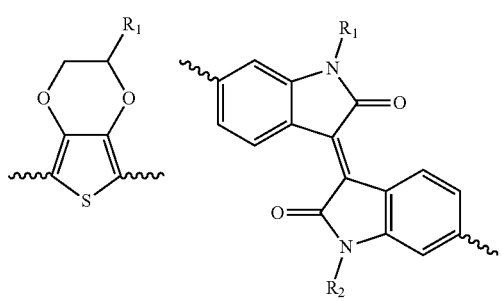
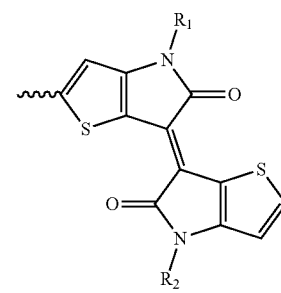
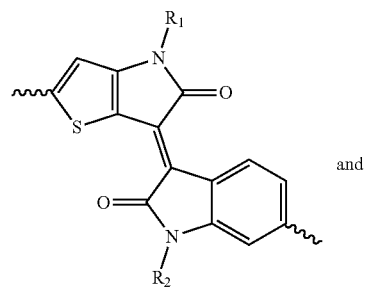
and
-continued
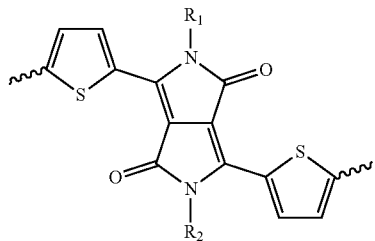
wherein the wave line ~~~~ represent a connecting point of the polymer compound; wherein the blocks of A, B or C are not in any particular order; and
wherein B is incorporated into the polymer compound using a compound selected from a group comprising of:
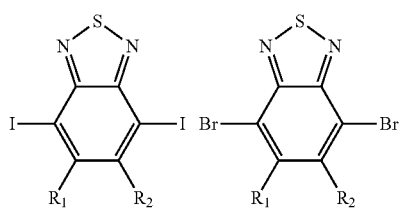
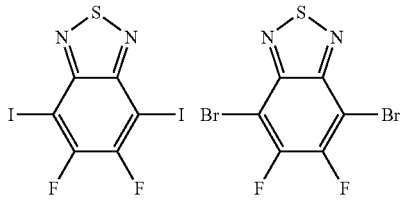
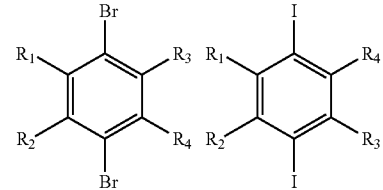
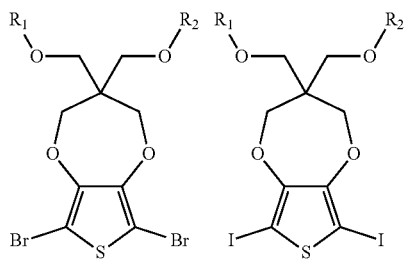
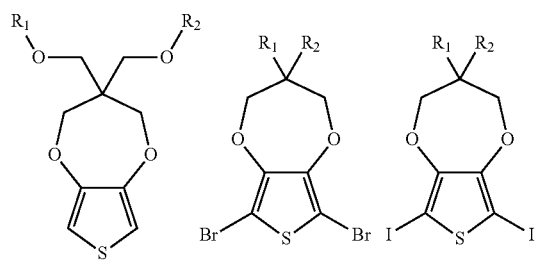

-continued
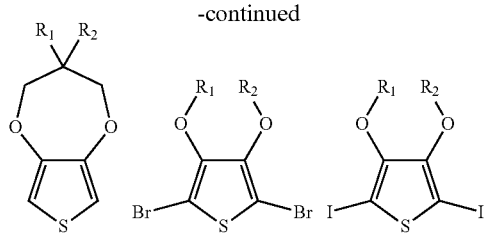
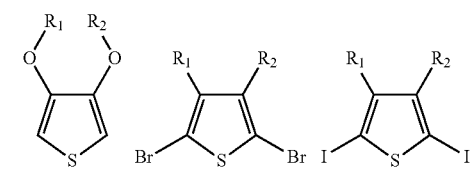
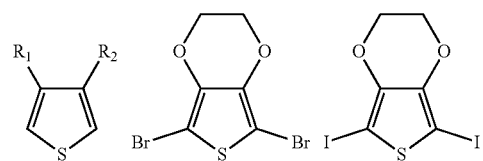
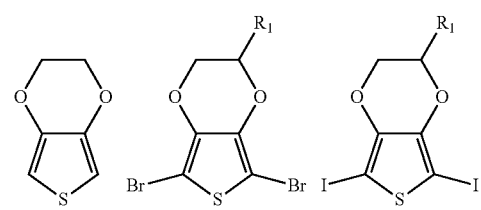
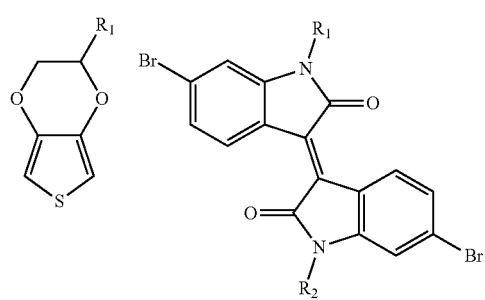
-continued
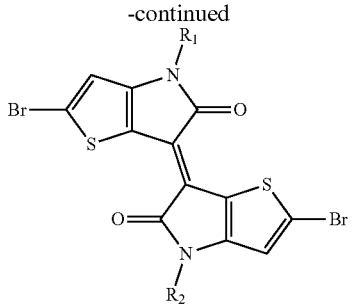
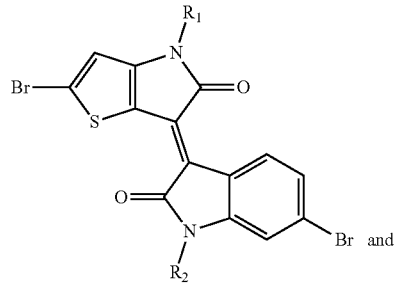 and
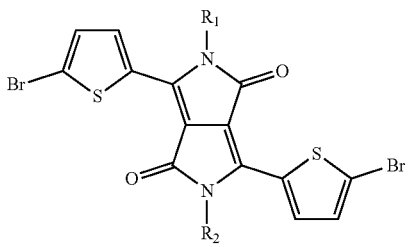
wherein each of $R_1$, $R_2$, $R_3$, $R_4$ is selected from one of hydrogen, C1-C30 alkyl, C2-C30 alkenyl, C1-C30 alkynyl, C2-C30 alkylcarbonyl, C1-C30 alkoxy, C1-C30 alkoxyalkyl, or C1-C30 alkoxycarbonyl.
11. The polymer compound of claim 10, wherein the polymer compound has a formula of:
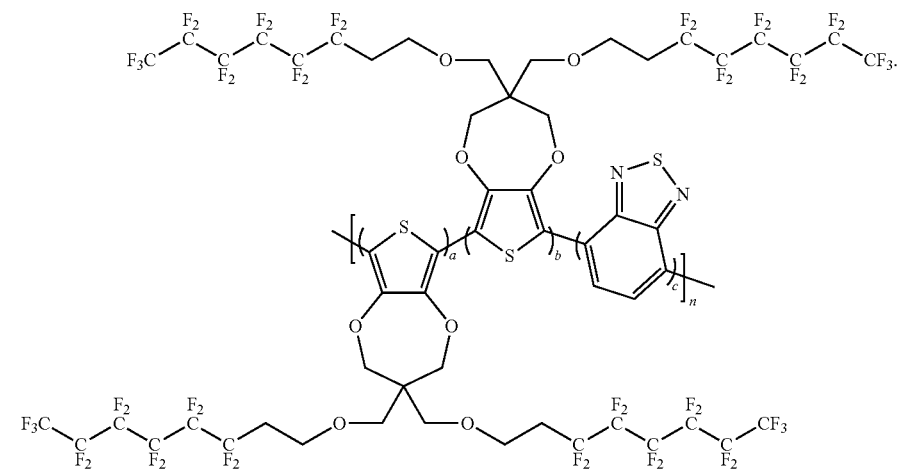

12. A device incorporating the compound of one of claims 1-11.

* * * * *

UNITED STATES PATENT AND TRADEMARK OFFICE
CERTIFICATE OF CORRECTION

PATENT NO. : 10,899,731 B2
APPLICATION NO. : 16/586148
DATED : January 26, 2021
INVENTOR(S) : Liyan You and Jianguo Mei It is certified that error appears in the above-identified patent and that said Letters Patent is hereby corrected as shown below:

In the Claims

In Claim 10, Column 43, Line 16:
"compound having comprising a formula" should read -- compound having a formula --.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*